(12) United States Patent
Gottlieb et al.

(10) Patent No.: US 8,326,653 B2
(45) Date of Patent: Dec. 4, 2012

(54) METHOD AND APPARATUS FOR ANALYZING PATIENT MEDICAL RECORDS

(75) Inventors: Meir Gottlieb, Baltimore, MD (US); Sheldon H. Gottlieb, Baltimore, MD (US); Gabriel Weisz, Baltimore, MD (US)

(73) Assignee: Nuance Communications, Inc., Burlington, MA (US)

( * ) Notice: Subject to any disclaimer, the term of this patent is extended or adjusted under 35 U.S.C. 154(b) by 2059 days.

(21) Appl. No.: 10/378,748

(22) Filed: Mar. 4, 2003

(65) Prior Publication Data

US 2004/0176979 A1 Sep. 9, 2004

(51) Int. Cl.
G06Q 10/00 (2006.01)
G06Q 50/00 (2006.01)
G06Q 40/00 (2006.01)

(52) U.S. Cl. ..................................... 705/4; 705/2; 705/3
(58) Field of Classification Search ................... 705/2–4
See application file for complete search history.

(56) References Cited

U.S. PATENT DOCUMENTS

| | | | |
|---|---|---|---|
| 5,496,991 A * | 3/1996 | Delfer et al. | 235/379 |
| 6,283,761 B1 * | 9/2001 | Joao | 434/236 |
| 6,330,357 B1 * | 12/2001 | Elmenhurst et al. | 382/175 |
| 6,343,271 B1 * | 1/2002 | Peterson et al. | 705/4 |
| 6,529,876 B1 | 3/2003 | Dart et al. | |
| 6,587,945 B1 | 7/2003 | Pasieka | |
| 6,603,464 B1 * | 8/2003 | Rabin | 345/179 |
| 2002/0019754 A1 * | 2/2002 | Peterson et al. | 705/4 |
| 2002/0194035 A1 * | 12/2002 | DiRienzo | 705/4 |
| 2003/0083903 A1 * | 5/2003 | Myers | 705/2 |
| 2005/0177396 A1 | 8/2005 | Gottlieb et al. | |

OTHER PUBLICATIONS

Online Solution Improves Hospitals' Financial Health, PR Newswire, New York, Feb. 24, 2003, p. 1.*

* cited by examiner

*Primary Examiner* — Jason Dunham
*Assistant Examiner* — Amber Altschul
(74) *Attorney, Agent, or Firm* — Wolf, Greenfield & Sacks, P.C.

(57) ABSTRACT

A medical form is marked by a clinician during a patient/clinician encounter to generate a record with information related to a current complaint. The form is partitioned into several regions related to patient history, examination and medical decision, respectively. The form is automatically analyzed and using the locations of the marks on the form and a predetermined set of rules, a billing code is generated. The billing code determines the fee to be paid to the clinician or health provider.

15 Claims, 3 Drawing Sheets

METHOD AND APPARATUS FOR ANALYZING PATIENT MEDICAL RECORDS

RELATED APPLICATIONS

None

BACKGROUND OF THE INVENTION a. Field of Invention

This invention pertains to a method and apparatus for reviewing, preferably automatically, patient medical records, and to generate a characteristic code for each record that is related to the health of the patient and to medical services provided by a clinician for the patient during a particular encounter. The method and apparatus is particularly useful for generating codes for generating bills to the patient or for a third party, such as a governmental or private health insurance organization.

b. Description of the Prior Art

In this application, the term 'encounter' is used to refer to any event between a patient and a clinician associated with the health of a patient. Thus, an encounter may occur at a clinician's office, in the emergency room of a hospital, at a normal bed in the hospital, in an ICU unit, etc. It is well established that any encounter must be memorialized in a corresponding medical record. These records are very important for every person and organization involved, including the patient, the clinician, the facility (e.g., hospital) where the encounter occurs, insurance companies, health organizations and so on. The record provides the clinician with information for providing immediate, as well as future care for the patient; it provides information for other clinicians in a simple and effective mater to insure consistence and continuity and to avoid duplication during subsequent encounters; it provides information useful for monitoring the performance of the clinician and/or health facility; it provides information that can be collected from several locations for statistical analyses used in research and education.

Importantly, the record is the source used to generate billing and to support claims review. The services requiring medical records are generally referred to as Evaluation and Management (or E/M) Services.

The content of medical records has been studied extensively, and has been the subject of guidelines promulgated by several organizations, including the AMA and the CMS (Center for Medicare and Medicaid Services). For instance, the '1995 Documentation Guidelines for Evaluation & Management services' ('Guidelines') is promulgated by the CMS and widely used throughout the United States. The actual form of the record may vary from one hospital to another and even from one department to another, within the same hospital; however, as promulgated by the guidelines, a typical record must include a description of the history of the patient, the examination performed by the clinician, and the medical decision reached by the clinician. Each of these components may include a number of topics and subtopics, depending on the illness of the patient and the severity of the illness.

Importantly, CMS also publishes a set of regulations that defines a payment scale to the clinician based on the record. These regulations must be used by any entity applying to the CMS for a payment. The same or similar regulations may be used by other health insurance organizations.

Thus the use of a comprehensive and standardized record has become not only desirable, but mandatory in the field of health care. Typically, the record is generated by the clinician by filling out a standardized form. This form may be several pages long. Ideally, the clinician, or his assistant, can fill in the form during or immediately after the encounter. Alternatively, the clinician dictates the required information, and the record is generated from the transcribed information. In real life, the generation of the record is delayed by several days or even weeks. Once the record is generated, it is stored and/or disseminated as required.

As discussed above, one important function of the record is to provide information that may be used for the generation of the bills. More specifically, the record itself must be used to generate billing code which then determines how much the clinician or the health care facility gets paid by an insurance organization. In addition, the record must be preserved to provide backup for the bills in case of an audit. In most instances the rules or regulations governing billing of health insurers and other organizations, such as Medicare and Medicaid, are very complicated, and they are related to the level of complexity of the services provided for each component of the report. Therefore, the clinician or his assistant may make an educated guess at what the code should be. This approach is not very productive because, if the wrong code is used, the amount paid by the insurance organization is either too high, and the clinician may be liable for a penalty, or too low, and therefore unprofitable.

Large organizations may employ special personnel whose function is to review each record and generate therefrom the appropriate billing code. This approach is expensive, and since the personnel has no medical training, mistakes can be made anyway.

It has also been suggested that billing codes be generated using special computer programs, for example from Medinotes Corporation. However, these programs are always menu or template driven and require a long time to fill out, time that the clinician does not have. Moreover, data entry is performed on a keyboard, and most clinicians do not want to rely on keyboards. Finally, the programs are very complicated and require long and intensive training periods. One such system is disclosed in U.S. Pat. No. 5,483,443, incorporated herein by reference.

OBJECTIVES AND SUMMARY OF THE INVENTION

In view of the above disadvantages of the prior art, it is an objective of the present invention to provide an easy, simple, and user-friendly method and apparatus of generating billing codes.

A further objective is to provide a method and apparatus capable of analyzing a record in an existing media or format and to generate a report or other output associated with and descriptive of the record.

Yet another objective is to provide a method and apparatus that is flexible so that it can be modified quickly and easily to records having new and unusual formats.

Other objectives and advantages of the invention shall become apparent from the following description.

Briefly, for every encounter between a patient and a clinician, a record is generated by the clinician with information associated with the patient's current complaint. The information is normally stored on a pre-printed form with regions associated with the various phases of the encounter, including patient history, physical examination and medical decision. Each region includes several subdivisions. The clinician enters markings (which may consist of Xs, checkmarks, alphanumeric text, etc.) on the form. The form can be generated electronically on an electronic device such as tablet PC or a hand-held device, and the clinician can enter his marks (and thereby populate the form) directly on the electronic device According to this invention, in order to generate a billing code, the form is electronically scanned to detect the location of the markings within each region. Then a set of predetermined rules is used on the markings to generate a billing code. More particularly, a parameter is derived for each region, based on, for example, the number of markings, or rows with markings that the clinician used. The billing code is then determined from these parameters. The billing code is then forwarded to a medical insurance company which uses a preset scale to determine the fee paid to the clinician or associated health care provided.

DETAILED DESCRIPTION OF THE INVENTION

Figure 1:
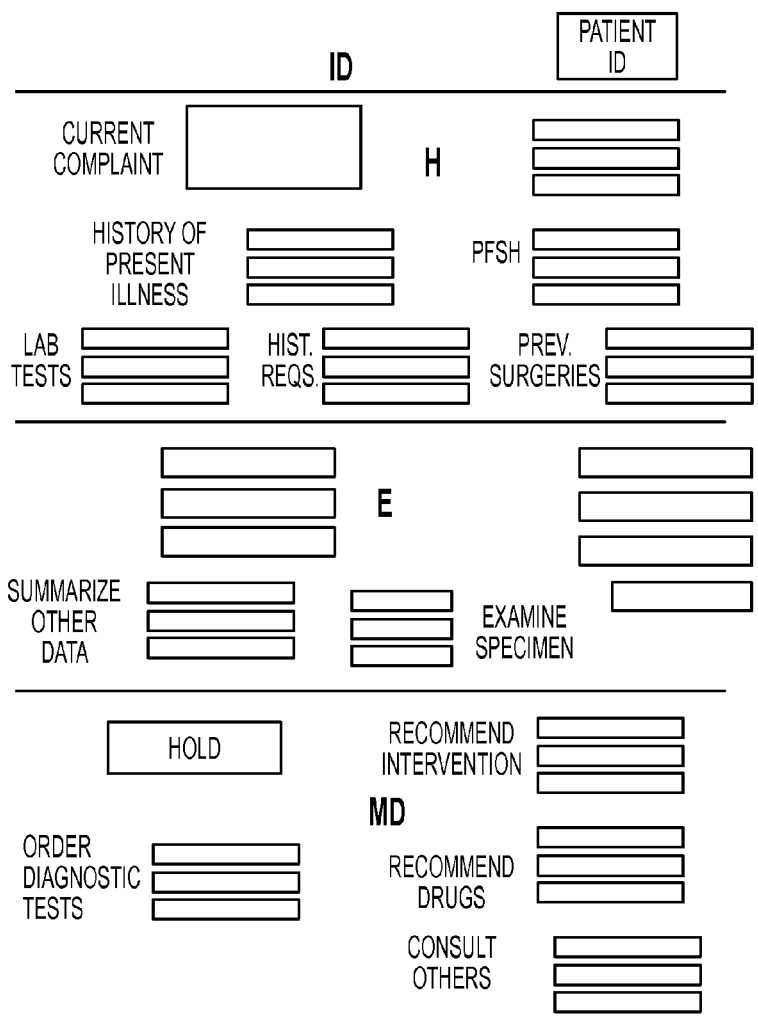
FIG. 1 shows a somewhat abbreviated form used to generate a record of a patient encounter.

FIG. 1 shows a form used by a clinician to document an encounter with a patient. For the sake of simplicity, the form has been abbreviated, it being understood that in actuality, more comprehensive forms are used. As promulgated by the AMA, a typical encounter between a clinician and a patient consists of three phases: establishing the history, performing an examination and making a medical decision. The purpose of the form shown in FIG. 1 is to enable the clinician to capture information associated with each of these phases, thereby generating the record for the encounter. Once this record has been completed, it can be stored for future review, disseminated to other clinician as necessary, used to generate a billing code, etc. The regulations promulgated by the CMS and other organizations, require that the billing codes be related to each phase of the record generating process, as described in detail below.

Therefore, the form of FIG. 1 is considered to have four areas; ID, H, E and MD. The area ID includes patient information such as name, address, physician, ID number, etc. Area H is dedicated to information related to patient history. Area E is dedicated to information related to the physical examination of the patient and area MD is related to the medical decision.

Each of the last three areas are broken down into subdivisions. The number and physical size of these subdivisions can vary depending on a large number of factors including the type of the patient's illness, internal policies of the clinician and/or associated health care organization etc. For example, the history area H is normally partitioned into four subdivisions: current (or chief) complaint, history of present illness (HPI), review of systems (ROS) and past, family and/or social history (PFSH).

The examination area E is partitioned into subdivisions covering the major organs of the body, as shown.

Finally, at the end of the encounter, the clinician makes a medical decision for treating the patient. This decision can be classified as hold (i.e. do nothing), recommend surgical intervention, recommend drug treatment, or recommend further diagnostic testing.

The form provided to the clinician is preprinted with legends that identify the various areas and their subdivisions. Blank boxes or rows are then provided in which the clinician enters the requested information, if any. Some entries may consist simply of check marks, X's etc., while other entries may consist of written words and sentences.

It is important to note that, within each area, the amount of information entered by the clinician and the number of subdivisions within each zone in which he enters the information is directly related to the amount of effort he has to spend in order to complete the record, and, accordingly, it bears a direct relation to the billing code.

Figure 2:
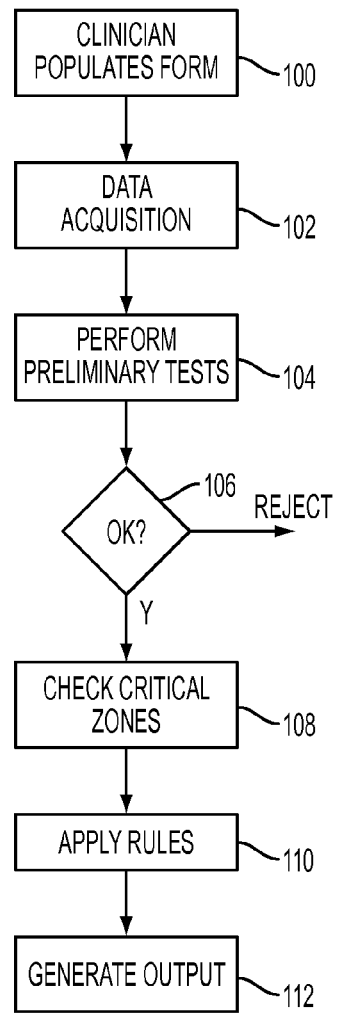
FIG. 2 shows a flow chart of the method used in accordance with this invention to generate a desired output, such as a billing code using information from the form of FIG. 1.
Figure 3:
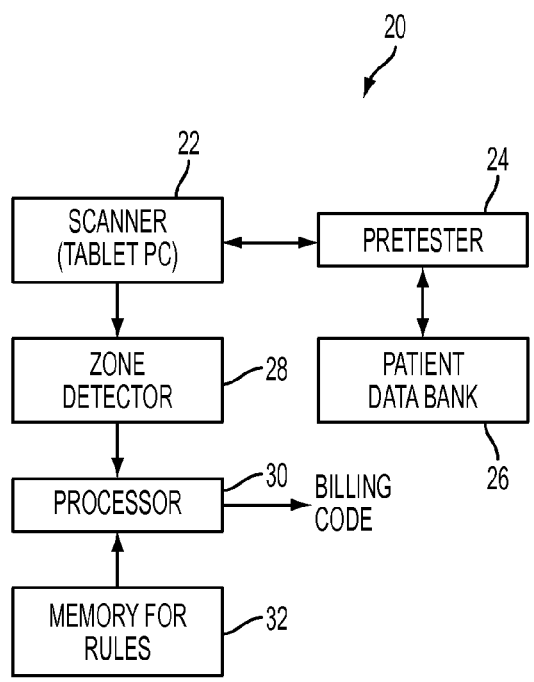
FIG. 3 shows a schematic diagram of a system used for implementing the method.

The process for generating a billing code is described generally in the flow chart of FIG. 2 while FIG. 3 shows a system 20 for implementing the process. In step 100 the clinician obtains a form, such as the one shown in FIG. 1, and populates it during the encounter. As discussed above, this process includes asking the patient questions, performing a physical examination, considering available data such lab and test results and then making a medical decision. If the form is provided on paper, then this step is performed by writing on the form with a pen or a pencil, and when completed the form is scanned using the scanner 22 in FIG. 3. In step 102 data corresponding to the scanned form is acquired.

In FIG. 2 step 104 a set of preliminary tests is performed by the pretester 24 to insure that the form has been filled out properly and that the patient has been correctly identified. For example, the pretester 24 may determine that at least one zone in each area of the form has been marked. The pretester 24 may also be determine if the patient has been correctly identified. For this purpose a bar code strip may be affixed to the ID zone. Alternatively, patient ID information may be typed in initially, and then the pretester 24 may use an OCR scheme to convert the markings in the ID zone to obtain the patient information found in the zone. The pretester 24 then accesses a patient data bank and compares the patient ID as recorded on zone ID with information from the patient data bank. If there is a discrepancy, the form may be rejected or a message may be generated to identify the problem.

In step 106 the pretester 24 makes a determination whether the process should continue or the form should be rejected.

If the process continues, then in step 108, the data from the scanner 22 is passed to a zone detector 28. This zone detector identifies the critical zones on the form and the various subdivisions in each zone and generates an indication of which of the respective subdivisions has any markings at all. This information is passed on to a processor 30. In step 1 the processor 30 accesses the applicable rules for billing codes. This rules are stored in a memory 32. The processor then applies the rules to the data received from the zone detector 28 and then generates an output in step 112, preferably in the form of a billing code. This output may be displayed on a screen, printed, or transmitted directly to an automated billing system.

Several different schemes may be used to recognize whether the clinician has made any entries into a critical zone, or not. For example, the form may be printed using ink of one color, and the clinician can use an ink of a different color to make his entries. The zone detector 28 can then perform an analysis which critical zones have been marked with the designated color.

Alternatively, a computer operator can fill out a computer based form (via a thick application or a web page), selecting the zones in which there were entries. A computer program on processor 30 can then perform an analysis of the scanned-in data and correlate the scanned-in data with an internal model of the form via a combination of well known machine vision (edge detection, huff transforms, snakes for stroke detection, etc) techniques to determine which data were inputted into which zone.

It is believed that initially most clinicians will prefer to mark up the forms manually. However, eventually, they may find it more advantageous to use some form of automated data acquisition, such as a tablet PC. In this latter case, in the system 20, the scanner 22 is replaced by the tablet PC which automatically generates in INK format or other similar formats an indication of what information has been entered by the clinician and on what part of the form. (An electronic version of the form is displayed by the PC tablet). This electronic data is then analyzed by the zone detector 30 to determine which critical zones have been used by the clinician to generate the record. In this embodiment, the PC tablet controls that store the "Ink" can prevent the user from performing a single stroke that crosses the boundary between zones, resulting in absolute knowledge of which zones have been used.

Alternatively, on a tablet PC, the user can be allowed to write anywhere on the form using ink, and then the application can compare what areas were written in predefined regions of the form. For example, if the form was represented in pixels on the screen, the processor could know where the fields are based on rectangles defined by the upper left hand corner and the lower right hand corner in pixels. For example Field 1 might be defined as (1,1) to (100,20) and Field 2 might be defined as (1,22) to (100,42). The processor could then use the Ink ActiveX controls provided by Microsoft to determine in which fields entries were made by the user.

In FIG. 3, the pretester 24 and zone detector 28 are shown as separate and distinct elements for the sake of clarity. However it should be understood that the functions of these elements may be performed by software on the processor 30. Moreover, if a PC tablet is used, its processor may be used to perform either some, or all of the functions of the pretester 24, the zone detector 28 and even the processor 30.

Once the processor 30 analyzes the various zones and subdivisions of the record, it then determines the billing code in accordance with the rules stored in memory 32. Some typical rules for generating billing codes shall now be described, it being understood that the invention is not limited to these rules but is applicable to other rules as well.

The commonly used '1995 Documentation Guidelines for Evaluation & Management Services' provide several classifications for each of the three phases of a patient encounter. History is provided with four classifications that are dependent on the following factors: History of Present Illness (HPI), Review of Systems (ROS) and past, family and social history (PFSH). The four classifications are defined as follows:

| HPI | ROS | PFSH | CLASSIFICATION |
|---|---|---|---|
| Brief | n/a | n/a | PROBLEM FOCUSED |
| Brief | Problem Pertinent | n/a | EXPANDED PROBLEM FOCUSED |
| Extended | Extended | Pertinent | DETAILED |
| Extended | Complete | Complete | COMPREHENSIVE |

Typical forms include several HPI rows for entering information characterizing the present complaint, such as location, quality, severity, duration, timing, context, modifying factors, signs and symptoms, and so on. The number of such rows can be anywhere from 0 to 8. The difference between Brief and Extended HPI is dependent on the amount of detail required to define the respective clinical problems, or in terms of the actual forms, the number of rows on which information has been entered. In the present invention, the HPI factor is determined by the number of rows that have entries. For example, if a form has a total of 8 entries (on 8 respective rows), the number of rows is counted and if this number is less than a predetermined number (for example 4 then the HPI factor is designated as being 'Brief'. Otherwise the HPI factor is designated as being 'Extended'.

Similarly, a typical form has a number of entries or rows for the ROS factor. A typical form may have fourteen such rows. Again, to determine the ROS factor, in the present invention the number of rows with entries is counted. Typically, for up to 3 entries the ROS factor is designated as 'Problem Pertinent', for between 4 and 9 entries the ROS factor is designated as 'Extended' and 10 or more entries are designated 'Complete.'

Finally, typically three or more rows are dedicated for PFSH, covering respectively, past medical history, family medical history and social history. The number of entries are counted and at least one entry is designated as pertinent and two or more entries are designated as 'Complete.'

Figure 4:
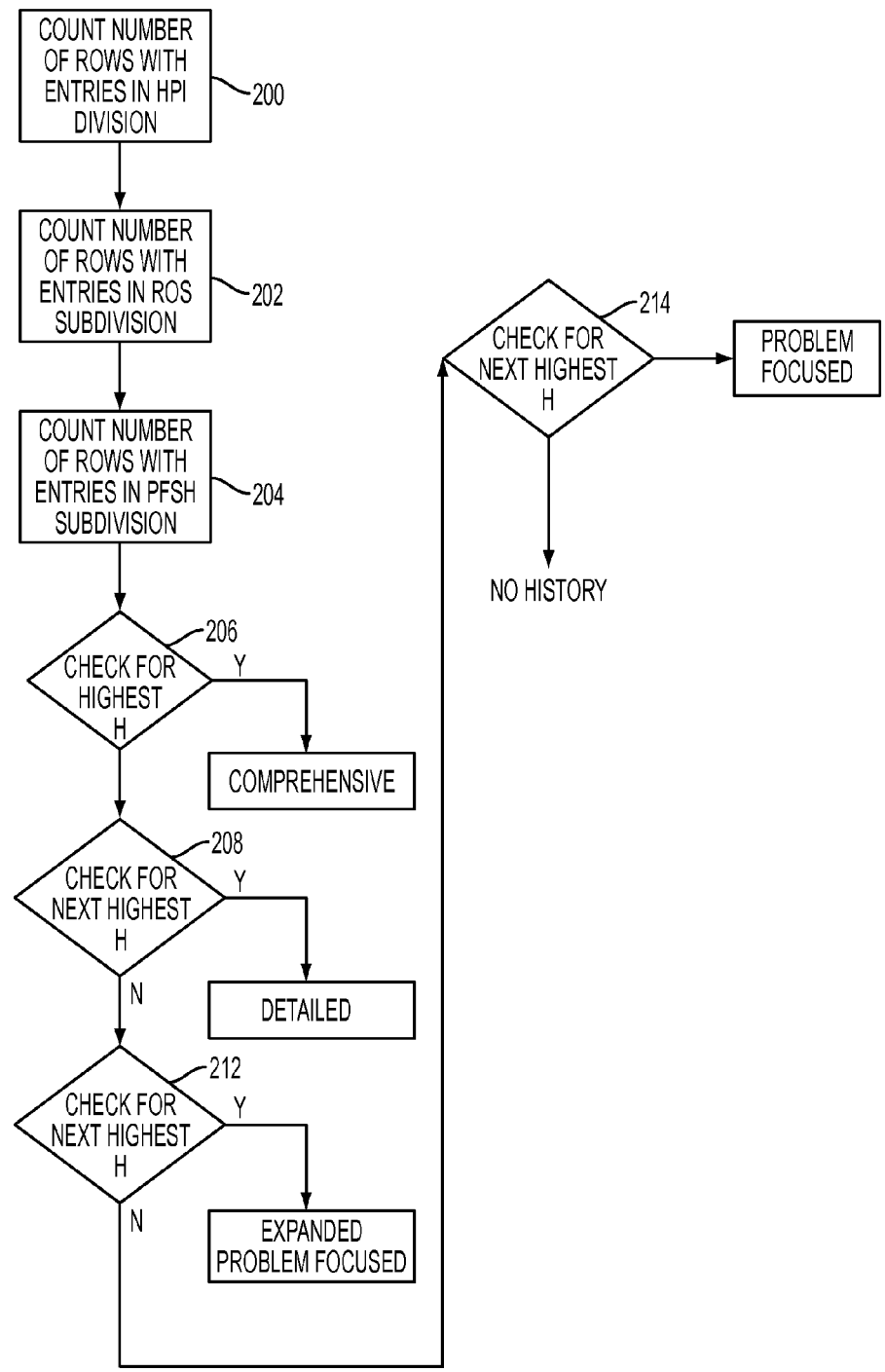
FIG. 4 shows a flow chart for determining the history parameter.

Thus, for the form of FIG. 1 the decision for determining the type of history is performed as illustrated in FIG. 4 and is reduced to counting the number of rows in each subdivision of zone H. In steps 200, 202 and 204 the number of entries for rows in each of the subdivisions HPI, ROS and PFSH is counted.

Generally speaking, the History parameter can be determined by looking at the number of elements or rows completed for the HPI, ROS, and PFSH subdivisions and then applying the relevant rules to these numbers. All the rules are based on minimums. The process starts by looking at the minimum requirements for the highest level of History classification. If these requirements are met, the History parameter is set and the process for determining this parameter is complete. If the requirements for the highest history classification are not met, the level below it is examined. The levels are defined in descending order as: Comprehensive, Detailed, Expanded Problem Focused, Problem Focused, and No History.

More specifically, as indicated in FIG. 4, the following steps are first performed to calculate the history parameter: Step 200—count the number of rows in the HPI subdivision. Step 202—count the number of rows in the ROS subdivision. Step 204—count the number of rows in the PFSH subdivision. Step 206—check if there is at least 4 elements or rows in the HPI subdivision, at least 10 elements in the ROS, at least 2 elements in the PFSH. If so, classify the history as comprehensive. Step 208—check if there is at least 4 elements in the HPI, at least 4 elements in the ROS, at least 1 element in the PFSH. If so, classify the History parameter as detailed. Step 210—check if there is at least 1 Element in the HPI, and at least 1 element in the ROS. If so, classify the history parameter as expanded problem focused. Step 212—check if there is at least 1 HPI, If so, classify the history parameter as problem focused. If none of these criteria are met, then a 'no history' classification is set.

Alternatively, the determination of the history classification is reversed. First a test is performed for the lowest classification, then the next higher classification, and so on.

The examination zone E is analyzed using the same general principles. The examination is divided into five levels (from highest to lowest): Comprehensive, Detailed, Expanded Problem Focused, Problem Focused, and No Exam. The level of the Exam is based on the number of body areas or organ systems examined and the completeness of the examination of those body areas or organ systems. Zone E in the form is divided into regions and sub regions. Exam regions include (but are not limited to): Constitutional, Eyes, Head/Mouth/Teeth, Chest, Cardiovascular, GI, MSK, GU, Derm, Neuro, Psych, and Blood/Lymph. These regions are then divided into sub regions. For example, the section for Cardiovascular is further divided into regions for all the various measurements and pulse readings that a Cardiologist would measure during a cardiovascular exam. The number of regions determines the number of organ systems examined. The number of sub-regions completed for a body area or organ system determines the extent of the examination of that body area or organ system. For each type of region (Eyes, Chest, etc.) there are a 2 thresholds defined to determine 3 levels: Brief<=T1<Detailed<=T2<Complete. If the number of sub-regions written in for a region is less that or equal to T1, then the Exam of that region is Brief. If the number of sub-regions written in is >T1 and <=T2, then the exam of that region is Detailed. If the number of sub-regions written in is >T2 then the exam of that region is complete. These two thresholds are defined for each body area/organ system. Furthermore, the division into sub-regions of the regions of an organ system/body area can be tailored or the situation that the form will be used in. For example, a cardiologist might have the cardio-vascular regions subdivided more than an Ophthalmologist, while the Ophthalmologist would more likely have the Eyes region broken down into more sub regions. However, in the case of General Medicine, it is possible that all body areas/organ systems are divided into many sub regions. The choice to not subdivide regions would be for specialties where it is unlikely that they would perform a comprehensive exam of a particular body area/organ system.

To determine the level of the examination parameter, the process starts looking for the highest level. If the criteria is met, the E classification is set at that level. Otherwise the next level of the exam is checked. For each region (corresponding to a single body area/organ system) in the Exam, the region is classified as Brief, Detailed, or Completed based on the threshold system described above.

If there is a Complete examination of a single region, then exam is considered Comprehensive. If at least 8 regions are Brief, the exam would also be considered Comprehensive.

If at least 2-7 regions were Detailed, the Exam would be considered Detailed.

If at least 2-7 regions were Brief, the exam would be recorded Expanded Problem Focused.

If at least one regions was Brief the exam is recorded as Problem Focused. (7) Otherwise, the Exam is marked as No Exam.

The last parameter to be considered is the medical decision. This parameter is dependent on four factors: the number of diagnoses or management options applicable to the respective chief complaint, the amount and complexity of the data reviewed by the clinician to make his decision and the risk of complication or morbidity. The four classifications for this parameter and their definition is as follows:

| NUMBER OF DIAG. OPTIONS | AMOUNT OF DATA | RISK OF COMPLICATION | DECISION MAKING |
| --- | --- | --- | --- |
| Minimal | Minimal | Minimal | STRAIGHT-FORWARD |
| Limited | Limited | Low | LOW COMPLEXITY |
| Multiple | Moderate | Moderate | MOD. COMPLEXITY |
| Extensive | Extensive | High | HIGH COMPLEXITY |

It has been suggested that a point system be used for determining the values of the first two factors. More specifically, the following table illustrates a point system for the first factor:

| CURRENT COMPLAINT | VALUE ASSIGNED | POINTS | SUBTOTAL |
| --- | --- | --- | --- |
| Old- Self-limited/minor | XXX XXX | 1 1 | X X |
|  | 2(max) |  |  |
| Old- Stable/improved | XXX | 2 | X |
| Old-worsening |  | 3 | X |
| New-no additional work | XXX 1 | 4 | X X |
| New-followup planned | 1 |  | X |
| TOTAL |  |  | T1 |

The points are determined based on fields completed in the form. In the form there is space for multiple problems. For each problem there is space for the provider to indicate whether the problem is a new problem or an established problem, and whether the problem is getting worse, stable, getting better, or self-limited/minor. Additionally there is space on the form to indicate the treatment plan for the problem. Alternatively, the treatment plan could be determined from other parts of the form indicating orders (such as medication, tests, or surgery). When the form is scanned, based on the boxes filled in, the processor classifies the problem as one of the 5 rows illustrated above and assigns the appropriate number of points. The points are then tallied across all the problems.

In order to determine the amount and complexity of data to be reviewed, the form is scanned to determine what other information he clinician has reviewed or ordered, or other actions taken by the clinician as part of the encounter. For example, as part of an encounter, the clinician may receive various test results based on tests conducted prior to the encounter. The clinician reviews the tests, and marks on the form the test results that he thinks are pertinent. More specifically, many forms include a subdivision (shown in FIG. 1 in the history area H) with a plurality of rows, each row indicating a test (e.g. lab tests, including blood tests, urine tests, etc., radiology tests, catscans, etc.). The clinician enters a notation on the rows corresponding to the tests that he has reviewed. Conversely, if insufficient information is available, the clinician orders some tests. This request is entered on the form in the MD area.

In some instances, the clinician may decide to consult with another clinician who has seen the patient, has performed one or more of the tests, or for some other reason. A subdivision is provided on the form, for example in the history area H, as shown, providing a row for each such discussion.

Other activities that the clinician may take include ordering old history and records, performing additional independent review of the specimen etc. These additional activities are also noted on the form.

As discussed above, during processing, the form is reviewed by essentially counting all the relevant rows on which entries for the various activities are marked. Some activities, such as the independent review of specimen, may be more labor intensive and so, during counting of the rows, a weighting system can be used so that entries in certain rows are accorded more relevance then entries from other rows. Once these rows are counted, a value is assigned to data complexity factor.

Next, the risk of complication is classified. Many complaints are associated with well known levels of complications and therefore can be readily classified by the clinician. An appropriate row can be provided for this purpose, for example as part of the current complaint subdivision.

For other encounters, the risk of complications is classified from other information readily available from the record. For example, as part of history, the clinician requests information about the medication that the patient is taking and/or surgery or other procedures that have been performed. The clinician records this information by marking the appropriate rows of the drugs and surgery subdivisions, respectively. Moreover, the clinician can also recommend surgical intervention and/or drugs by marking the relevant subdivisions of the MD area. It is well known in the medical field that taking certain drugs or performing certain types of surgeries and other procedure are associated with certain risks of complications. The types of tests either performed prior to the encounter (and marked in the history area H) or ordered by the clinician (and marked in the MD area) are also indicative of the level of risks of complication. The form has space for tests that are pre-classified for Risk. For example, for a form used by Cardiology, there would be space on the form for information about Cardiac Catheterization, Electrophysiology (such as temporary pacing), EKG, Stress test, etc. If the clinician marked that he/she ordered a Cardiac Catheterization, the risk would be marked as Moderate.

Additionally the level of risk is dependent on the presenting problems. The provider can be asked to classify problems, self-limited/minor, stable chronic, acute uncomplicated, acute complicated, life-threatening. Based on the classification of the problem and the number of problems, the level of risk can be determined. For example, a single life-threatening problem such as an acute myocardial infarction is considered High Risk. Alternatively, possible problems can be listed on the sheet and circled by the clinician. In this way, the problem can be pre-classified to determine level of risk. This option in most attractive for specialties where there is a limited number of problems that the clinician is considering. A hybrid approach could be used where problems are listed and pre-classified, but the clinician is asked to classify problems that are not listed. This way the clinician simply circles the appropriate problem the majority of the time, but can easily write-in problems that are not on the list.

Preferably the level of risk of complication is determined either directly by the clinician, or is determined indirectly by reviewing the record for certain predetermined drugs, surgical (or other procedures) and tests.

As can be seen from the above discussion, the information required to classify each phase of an encounter is in most cases readily available from the record. In some cases additional subdivisions may have to be added to the standard form to insure that all the information required to classify each phase is properly entered. As an alternate, and possibly intermediate solution, some of the information can be obtained from additional sources. For example, if at the end of the encounter the clinician orders some additional tests to be taken and/or prescribes some medicine to the patient using some additional forms, these forms can be intercepted and reviewed as well, in the same manner as the record, to gather the additional required information.

Once the three phrases are properly classified, a billing code is readily generated by the processor in steps 110 and 112 of FIG. 2. Some typical billing codes are defined by the AMA as follows:

| HISTORY | EXAM | MED.DECISION | CODE |
| --- | --- | --- | --- |
| problem focused | problem focused | straightforward | 99201 |
| expanded problem focused | expanded problem focused | straightforward | 99202 |
| detailed | detailed | low complexity | 99203 |
| comp. | comprehensive | mod. complexity | 99204 |
| comp. | comprehensive | high complexity | 99205 |

To summarize, every encounter between a clinician and a patient must result in a record on a standardized form. The present invention analyzes the record to determine what part of the form has been marked by the clinician as part of generating the record. This information is then used to classify each phase of the encounter. Finally this classification is used to generate an appropriate billing code. Of course, it should be understood that the process may be used for additional purposes as well.

As described above, the process for generating a billing code involves detecting markings on a predetermined form and based on the number and location of the markings on the form, generating the code using a set of predetermined rules. However, it should be appreciated that the process is transparent to the actual content of the form.

While the invention has been described with reference to several particular embodiments, it is to be understood that these embodiments are merely illustrative of the principles of the invention. Accordingly, the embodiments described in particular should be considered as exemplary, not limiting, with respect to the following claims.

We claim:

1. An apparatus for generating a medical billing code from a populated form resulting from a patient/clinician encounter, said populated form having locations with marks, each mark having a respective content indicative of either information obtained by the clinician during the encounter about the patient or a physical condition of the patient, said marks being made by the clinician, comprising:
   a detector, comprising at least one processor, adapted to detect marks on said form, within predetermined zones defined thereon; and
   an analyzer, comprising the at least one processor, adapted to generate a medical billing code based on said number of zones with marks detected on said form and a predetermined set of rules, wherein said rules are independent on the content of the markings at the respective locations.

2. The apparatus of claim 1 wherein said form is hard-copy form and said detector includes a scanner that scans said hard-copy form.

3. The apparatus of claim 1 wherein said detector includes an electronic data collection device adapted to generate an image of said form and wherein said data collection device is adapted to detect said marks as they are entered on said electronic data collection device.

4. The apparatus of claim 3 wherein said electronic data collection device is a tablet PC.

5. The apparatus of claim 1 wherein each zone has respective locations and marks made at least at some of said locations, and wherein analyzer counts the number of marks in each zone, generates a respective parameter and operates said preselected set of rules on said parameters to generate said billing code.

6. The apparatus of claim 5 wherein said parameter is selected by said analyzer based on the complexity of a task performed by the clinician, said task being associated with the respective zone of said form.

7. The apparatus of claim 1, wherein said analyzer assigns a classification for each zone and determines said billing code by evaluating the classifications of said zones.

8. The apparatus of claim 7 wherein said zones include at least one zone dedicated to one of the patient's history of present illness, review of systems and past, family and social history.

9. The apparatus of claim 1 wherein the form includes at least one zone, said zone including several regions, each region including at least one subregion and reflecting the examination of one of a body organ and organ system of a patient, wherein said analyzer assigns a respective parameter for each region depending on how many subregions have markings, and wherein said analyzer further assigns said billing code based on the parameters from said regions.

10. A method of generating a billing code for an encounter between a patient and a healthcare provider, wherein during the encounter, the healthcare provider populates a form defining a history zone, an examination zone and a prognosis zone by making entries in several subdivisions within the respective zones, each entry indicating some information or patient condition as determined or obtained by the clinician, said method comprising:

using at least one processor, analyzing each zone to determine how much effort has the clinician spent in examining the patient during the respective zone, wherein at least in one zone, said analyzing includes counting the number of subdivisions within said one zone that have entries;

using the at least one processor, assigning a parameter to each zone based on said analysis, wherein in for at least one of said zone, said step of assigning is dependent on the number of subdivisions within that zone in which there are entries made by the clinician each said parameter being completely independent of any information associated with the entries in the respective zone;

using the at least one processor, generating a classification for said encounter indicative of the complexity of the encounter based on the parameters assigned to each zone; and using the at least one processor, assigning a billing code for the encounter based on said classification.

11. The method of claim 10 wherein said form further includes an identification zone with information identifying the patient, further comprising verifying the information in said identification zone before analyzing the remaining zones.

12. The method of claim 10 wherein said form includes a history zone, an examination zone and a medical decision zone.

13. The method of claim 12 wherein said history zone and said examination zone are each designated as being one of problem focused, expanded problem focused, detailed and comprehensive.

14. The method of claim 12 wherein said medical decision zone is designated as being one of straight forward, low complexity, moderate complexity and high complexity indicating the complexity of the diagnosis performed by the healthcare provider.

15. A method of generating a billing code for an encounter between a patient and a healthcare provider, wherein during the encounter, the healthcare provider populates a form defining a history zone, an examination zone and a prognosis zone by making entries in the respective zones, each entry indicating some information or patient condition as determined or obtained by the clinician, said method comprising:

using at least one processor, analyzing each zone to determine how much effort has the clinician spent in examining the patient during the respective zone;

using the at least one processor, assigning a parameter to each zone based on said analysis, wherein in for at least one of said zone, said step of assigning includes determining the number of entries made by the clinician in the respective zone, each said parameter being completely independent of any information associated with the entries in the respective zone;

using the at least one processor, generating a classification for said encounter indicative of the complexity of the encounter based on the parameters assigned to each zone; and using the at least one processor, assigning a billing code for the encounter based on said classification;

wherein said form includes a history zone, an examination zone and a medical decision zone, said history zone and said examination zone are each designated said respective parameter as being one of problem focused, expanded problem focused, detailed and comprehensive; and wherein the parameter for said medical decision zone is designated as being one of straight forward, low complexity, moderate complexity and high complexity indicating the complexity of the diagnosis performed by the healthcare provider.

* * * * *